United States Patent [19]

Cannata et al.

[11] Patent Number: 5,097,058
[45] Date of Patent: Mar. 17, 1992

[54] PROCESS FOR THE SYNTHESIS OF THE α-(-METHYL-ETHYL)-3,4-DIMETHOXYBEN-ZENE-ACETONITRILE

[75] Inventors: Vincenzo Cannata; Giancarlo Tamerlani, both of Pontecchio Marconi; Graziano Zagnoni, Vergato, all of Italy

[73] Assignee: Alfa Wassermann S.p.A., Alanno Scalo, Italy

[21] Appl. No.: 512,909

[22] Filed: Apr. 25, 1990

Related U.S. Application Data

[63] Continuation of Ser. No. 172,239, Mar. 23, 1988, abandoned.

[30] Foreign Application Priority Data

Apr. 8, 1987 [IT] Italy .................. 20019 A/87

[51] Int. Cl.$^5$ .......................................... C07C 253/20
[52] U.S. Cl. .................... 558/314; 549/549; 564/265; 568/442
[58] Field of Search ............ 549/549; 558/314; 564/265; 568/442

[56] References Cited

U.S. PATENT DOCUMENTS

| | | | |
|---|---|---|---|
| 3,261,859 | 7/1966 | Dengel | 260/465 |
| 3,415,866 | 12/1968 | Suh | 260/465 |
| 3,435,075 | 3/1969 | Glamkowski et al. | 549/549 |
| 3,997,608 | 12/1976 | Suh | 260/570.8 |
| 4,235,807 | 11/1980 | Fuhlhage | 558/314 |
| 4,456,562 | 6/1984 | Tamura et al. | 558/314 |
| 4,593,042 | 6/1986 | Liang | 514/523 |

FOREIGN PATENT DOCUMENTS

| | | |
|---|---|---|
| 986946 | 4/1976 | Canada . |
| 0165322 | 12/1985 | European Pat. Off. . |

OTHER PUBLICATIONS

Japanese Patent Publication J5 3092-732, 8-78 (Abstract).
Hungarian Patent HU T032-064-A, 6-84 (Abstract).
Chemistry Letters, pp. 1745-1748, 1987; Tokyo Institute of Technology.
British Pharmaceuticals, Photographic, pp. 6-7, vol. 9, No. 35, 8-1969.

*Primary Examiner*—C. Warren Ivy
*Assistant Examiner*—Ba K. Trinh
*Attorney, Agent, or Firm*—Birch, Stewart, Kolasch & Birch

[57] ABSTRACT

New process for the synthesis of the α-(1-m.ethylethyl)-3,4-dimethoxyacetonitrile of formula (I):

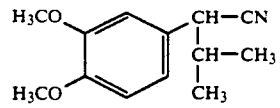

which is known as an intermediate in the synthesis of the drug internationally known as verapamil. The process starts from the isobutyryl-3,4-dimethoxybenzene of formula (II):

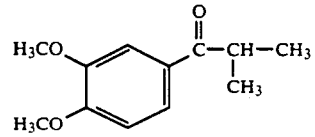

which, by means of the Darzens condensation, gives an epoxyester which, by alkaline hydrolysis and subsequent decarboxylation, gives the α-(1-methylethyl)-3,4-dimethoxybenzeneacetaldehyde. This product is reacted with hydroxylamine to obtain the corresponding oxime that, by dehydration, gives the nitrile of formula I.

4 Claims, No Drawings

PROCESS FOR THE SYNTHESIS OF THE α-(-METHYL-ETHYL)-3,4-DIMETHOXYBENZENE-ACETONITRILE

This application is a continuation of application Ser. No. 07/172,239 filed on Mar. 23, 1988, now abandoned.

BACKGROUND OF THE INVENTION

The α-(1-methylethyl)-3,4-dimethoxybenzeneacetonitrile is an intermediate useful in the preparation of a drug having coronodilator activity, internationally known as verapamil (INN), described in U.S. Pat. No. 3,261,859.

The synthesis of the α-(1-methylethyl)-3,4-dimethoxybenzeneacetonitrile has been described in many patents such a U.S. Pat. Nos. 3,415,866, 3,997,608 and 4,593,042, Canadian Patent 986946, Unexamined Japanese Patent Publication No. 78092732, European Publication No. 0165322 and Hungarian Patent HUT 032064.

The primary method, described in the Canadian and Hungarian Patents, in U.S. Pat. No. 4,593,042 and in the Unexamined Japanese Publication, consists in the alkylation of the homoveratronitrile by means of an isopropyl halide, in the presence of many kinds of alkaline agents and in different solvents. In U.S. Pat. Nos. 3,415,866 and 3,997,608, homoveratronitrile is reacted with acetone in the presence of sodium ethoxide and the resulting isopropylidene derivative is catalytically hydrogenated. Finally, in the above mentioned European Publication, the nitrile is obtained by reacting the α-(1-methylethyl)-benzylchloride with sodium cyanide.

DESCRIPTION OF THE INVENTION

An object of the present invention is a new method for the synthesis of the α-(1-methylethyl)-3,4-dimethoxybenzeneacetonitrile of formula (I):

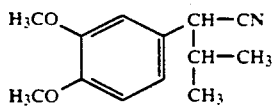

starting from the isobutyryl-3,4-dimethoxybenzene of formula (II):

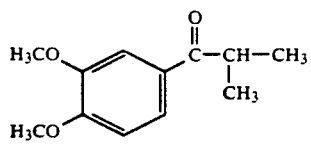

which undergoes the Darzens condensation with an alkyl ester of an α-haloacetic acid, in the presence of an alkoxide of an alkali metal or of sodium amide or sodium hydride, to give an α,β-epoxyester of formula (III):

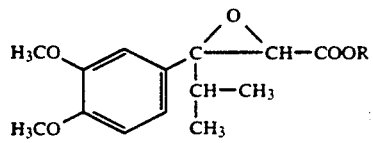

wherein R represents a straight or branched alkyl radical, containing from 1 to 6 carbon atoms, which, by alkaline hydrolysis, gives the alkali salt of the epoxyacid of formula (IV):

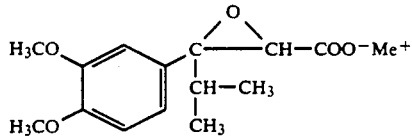

wherein Me+ corresponds to a cation of an alkali metal, preferably sodium or potassium, which, by decarboxylation, gives the α-(1-methylethyl)-3,4-dimethoxybenzeneacetaldehyde of formula (V):

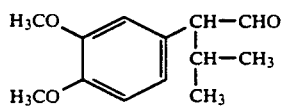

which, by treatment with hydroxylamine, gives the corresponding oxime of formula (VI):

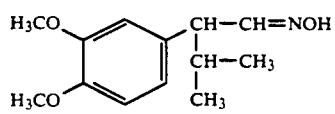

which is dehydrated, for instance in the presence of acetic anhydride and optionally of potassium acetate, to give the desired α-(1-methylethyl)-3,4-dimethoxybenzeneacetonitrile of formula I.

The process object of the present invention can be carried out without isolating and characterizing the various intermediates of the foregoing formulae; however, if it is desired, the various steps of this process can also be carried out separately, by isolating and characterizing the relevant intermediates.

The intermediates of formulae III, V and VI are new and therefore they constitute a further object of the present invention.

The process object of the present invention consists in reacting a molar equivalent of isobutyryl-3,4-dimethoxybenzene of formula (II):

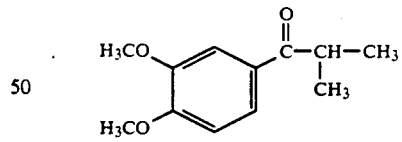

with from about 0.5 to about 5 molar equivalents of an α-haloester of formula (VII):

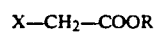

wherein X represents a halogen atom, preferably a chlorine atom and R represents an alkyl radical, straight or branched, containing from 1 to 6 carbon atoms, preferably methyl, ethyl or 2-butyl, in the presence of from about 0.5 to about 5 molar equivalents of a base selected from an alkoxide of an alkali metal of formula (VIII):

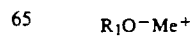

wherein Me+ represents the cation of an alkali metal, preferably sodium or potassium, and R₁ represents an alkyl radical, straight or branched, containing from 1 to 6 carbon atoms, sodium amide or sodium hydride. The preferably used bases are sodium methoxide, potassium tert-butoxide, sodium 2-butoxide and potassium 2-butoxide. The reaction takes place in a period of time comprised from about 1 to about 24 hours at a temperature comprised from about −25° C. to the boiling temperature of the reaction mixture. The reaction can be carried out with or without solvents. Suitable solvents are the aromatic hydrocarbons, preferably toluene, and the alcohols, straight or branched, containing from 1 to 6 carbon atoms, or their mixtures.

The glycidic ester of formula (III):

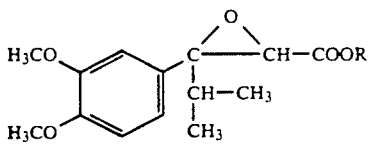

which forms during the reaction, wherein R has the above meaning, generally is not isolated but it is transformed into the alkali salt of the epoxyacid of formula (IV):

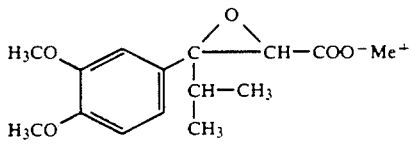

wherein Me+ corresponds to a cation of an alkali metal, preferably sodium or potassium, by means of an alkaline hydrolysis carried out by treating the solution containing the epoxyester of formula III with an alkali or an alkaline-earth base, preferably sodium or potassium hydroxide, for a period of time comprised from about 1 to about 12 hours at a temperature comprised from about 0° C. to the boiling temperature of the reaction mixture.

The salt of the epoxyacid of formula IV is then decarboxylated at a temperature comprised from about 20° C. to the boiling temperature of the reaction mixture for a period of time comprised from about 1 to about 16 hours. In this way the α-(1-methylethyl)-3,4-dimethoxybenzeneacetaldehyde of formula (V):

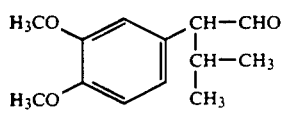

is obtained. By treating the aldehyde of formula V with a molar equivalent of hydroxylamine hydrochloride, at a temperature comprised from about 0° C. to the boiling temperature of the reaction mixture for a period of time comprised from about 0.5 to about 16 hours, the corresponding oxime of formula (VI):

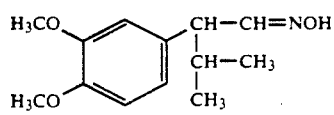

is obtained.

The desired nitrile of formula I is obtained by dehydrating the oxime of formula VI.

According to a preferred method, a molar equivalent of oxime of formula VI, optionally dissolved in a solvent selected among acetic acid, toluene, 2-butanol, acetonitrile and dimethylformamide, preferably in acetic acid, is reacted with from about 1 to about 4 molar equivalents of acetic anhydride optionally in the presence of from about 0.1 to about 2 molar equivalents of sodium acetate at a temperature comprised from about 20° C. to the boiling temperature of the reaction mixture for a period of time comprised from about 1 to about 48 hours, giving the α-(1-methylethyl)-3,4-dimethoxybenzeneacetonitrile of formula (I):

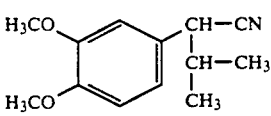

pure enough to be used without any further purification for the synthesis of the verapamil. However the nitrile can further be purified by distillation under vacuum or by crystallization.

In a preferred aspect of the invention, the α-(1-methylethyl)-3,4-dimethoxybenzeneacetaldehyde of formula V is not isolated from the reaction medium because, as it forms by decarboxylation of the salt of the epoxyacid of formula IV, it is reacted with hydroxylamine hydrochloride, thus directly transforming itself into the oxime of formula VI which is extracted from the reaction medium by means of an organic solvent, preferably toluene.

The $^1$H-NMR spectra of the products of formulae III, V and VI, which are to be new and that therefore constitute a further object of the present invention, have been carried out in CDCl$_3$ with a Bruker CXP 300 spectrometer, by using tetramethylsilane as reference substance. The symbols used have the following meaning: d=doublet; m=multiplet; q=quartet; s=singlet; t=triplet.

The examples below reported constitute an explanation of the present invention but are not to be considered as a limitation thereof.

EXAMPLE 1

3-(3,4-Dimethoxyphenyl)-3-(1-methylethyl)-oxiranecarboxylic acid, 2-butyl ester 31.2 Grams (0.15 moles) of isobutyryl-3,4-dimethoxybenzene are diluted with 150 ml of toluene, the solution is cooled to +5° C. and added with 42 g (0.375 moles) of potassium tert-butoxide. 53 Ml (0.375 moles) of 2-butyl chloroacetate are added in one hour to the reaction mixture while keeping it under stirring at the temperature of +10° C. for another 30 minutes. Then the reaction mixture is added with 200 ml of water and the two layers are separated. The aqueous phase is extracted with 50 ml of toluene and then is discarded, while the organic phases are collected together, washed three times with 100 ml of water, dehydrated on anhydrous sodium sulphate and lastly filtered on decolourizing earth. The filtrate is evaporated to dryness under vacuum to completely eliminate the solvent. The obtained oily residue is dissolved in 110 ml of hexane and left to crystallize at low temperature. The obtained precipitate is filtered and washed on the filter with cold hexane. The product is crystallized again from hexane thus obtaining 24 g of the 2-butyl ester of the 3-(3,4-dimethoxyphenyl)-3-(1-methylethyl) oxiranecarboxylic acid with a yield of 49.6%.

This product has m.p. = 36° C. ÷ 38° C. and its $^1$H-NMR spectrum presents characteristic resonance peaks to the following δ (expressed as p.p.m.): 0.6 ÷ 0.76 (m, 4H); 1 (m, 7H); 1.24 ÷ 1.40 (m, 3H); 1.97 (m, 1H); 3.66 (s, 1H); 3.86 (d, 6H); 4.63 (m, 1H); 6.82 (m, 3H).

EXAMPLE 2

α-(1-Methylethyl)-3,4-dimethoxybenzeneacetaldheyde 62.46 Grams (0.30 moles) of isobutyryl-3,4-dimethoxybenzene are dissolved in 300 ml of toluene, then the solution is cooled to +5° C. and added with 84 g (0.75 moles) of potassium tert-butoxide under nitrogen atmosphere. 104.6 Ml (0.75 moles) of 2-butyl chloroacetate are added to the reaction mixture during one hour while keeping the temperature between +5° C. and +10° C. 200 Ml of water are added after 4 hours stirring at room temperature, the aqueous phase is discarded while the organic phase is washed four times with 100 ml of water. The organic layer is then added in about one hour with a solution containing 51.3 g of 90% potassium hydroxide (0.80 moles) in 210 ml of methanol and the whole is kept under stirring for 3 hours at a temperature of about 30° C. After 210 ml of water are added, the phases are separated and the organic layer is extracted again with 50 ml of water and then is discarded. The aqueous phases are collected together and acidified to pH 4 by means of 32% (w/w) aqueous hydrochloric acid and the reaction mixture is heated to about 65° C. for 2 hours under stirring. After cooling to room temperature, the reaction mixture is brought to pH 9 by means of a 30% (w/w) aqueous solution of sodium hydroxide and is extracted first with 200 ml and then with 50 ml of toluene. The organic phases are collected together, washed with 100 ml of water, dried over anhydrous sodium sulphate, filtered and evaporated to dryness under vacuum.

The obtained oily residue is purified by treating it with n-hexane, obtaining 51 g of pure aldehyde, having m.p. = 52° C. ÷ 54° C., with a yield of 76.5% of the theoretical.

$^1$H-NMR Spectrum: characteristic resonance peaks are observed at the following δ (expressed as p.p.m.): 0.8 (d, 3H); 1.0 (d, 3H); 2.4 (m, 1H); 3.1 (q, 1H); 3.9 (s, 6H); 6.6 (d, 1H); 6.7 (q, 1H); 6.9 (d, 1H); 9.7 (d, 1H).

EXAMPLE 3

α-(1-Methylethyl)-3,4-dimethoxybenzeneacetaldoxime 44.44 Grams (0.02 moles) of α-(1-methylethyl)-3,4-dimethoxybenzeneacetaldehyde prepared in example 2 are dissolved in 180 ml of methanol, then 17.64 g (0.21 moles) of sodium bicarbonate are added and, finally, 14.60 g (0.21 moles) of hydroxylamine hydrochloride are added portionwise in 30 minutes. After stirring for an additional 30 minutes, 150 ml of toluene and 150 ml of water are added and the layers are separated. The aqueous phase is discarded. The toluene phases are collected together, washed with 50 ml of water, dried over anhydrous sodium sulphate, filtered and evaporated to dryness under vacuum. The oily residue is purified by treatment with heptane obtaining 43.40 g of oxime with a yield of 91.4%. An oxime sample crystallized three times from tetrachloroethylene, shows m.p. = 89° C. ÷ 91° C. and a $^1$H-NMR spectrum showing characteristic resonance peaks at the following δ (expressed as p.p.m.): 0.8 (d, 3H); 1.01 (d, 3H); 2.07 (m, 1H); 3.04 (t, 1H); 3.87 (2s, 6H); 6.76 (m, 3H); 7.54 (d, 1H).

EXAMPLE 4

α-(1-Methylethyl)-3,4-dimethoxybenzeneacetaldoxime

A suspension containing 37.4 g (0.33 moles) of potassium 2-butoxide in 50 ml of toluene is added with 20.8 g (0.10 moles) of isobutyryl-3,4-dimethoxybenzene and then 51 ml (0.36 moles) of 2-butyl chloroacetate are added in about one hour while keeping the temperature between 20° C. and 30° C.

After another hour of stirring at room temperature, a solution of 25.5 g of 90% potassium hydroxide (0.41 moles) in 105 ml of methanol is added and then the reaction mixture is kept 3 hours under stirring at room temperature. The reaction mixture is then added with 150 ml of water and the two layers are separated. The aqueous phase is twice washed with 50 ml of toluene while the organic phases are collected together, extracted with 50 ml of water and lastly discarded. The aqueous phases are collected together, added with 15 ml of acetic acid, heated to 65° C. and added with 6.95 g (0.10 moles) of hydroxylamine hydrochloride dissolved in 20 ml of water, in 30 minutes. After 1 hour at 65° C., the pH is brought to 4 by means of concentrated aqueous hydrochloric acid and the reaction mixture is kept under stirring for another hour. After cooling to room temperature, the reaction mixture is brought to pH 9 by means of a 30% (w/w) aqueous solution of sodium hydroxide and extracted three times with 50 ml of toluene each time. The toluene extracts containing the oxime are collected together, washed with 50 ml of water, dried over anhydrous sodium sulphate, filtered and evaporated to dryness under vacuum. By treating the oily residue with heptane, 21.6 g of oxime are obtained with a yield of 91% of the theoretical.

EXAMPLE 5

α-(1-Methylethyl)-3,4-dimethoxybenzeneacetonitrile 69.2 Grams (0.29 moles) of α-(1-methylethyl)-3,4-dimethoxybeneacetaldoxime are dissolved in 150 ml of glacial acetic acid and then are added with 38.8 ml (0.41 moles) of acetic anhydride.

An exothermic reaction takes place and, after the temperature has lowered to the room value, 24 g (0.29 moles) of anhydrous sodium acetate are added and the reaction mixture is heated at a temperature comprised between 80° C. and 85° C. for 5 hours. The reaction mixture is then evaporated under vacuum, the residue is treated with 200 ml of toluene and 150 ml of water and the resulting mixture is brought to pH 9 by means of a 30% (w/w) aqueous solution of sodium hydroxide. The layers are separated, the aqueous phase is twice extracted with 50 ml of toluene and then is discarded, the toluene phases are collected together, washed with 50 ml of water, dehydrated over anhydrous sodium sulphate and evaporated to dryness under vacuum obtaining an oily residue which is purified by distillation under vacuum; b.p. $_{2\ mmHg}$ 147° C. ÷ 148° C.

57.2 Grams of pure nitrile, having m.p. = 53° C. ÷ 55° C., are obtained, with a yield of 90% of the theoretical.

EXAMPLE 6

α-(1-Methylethyl)-3,4-dimethoxybenzeneacetonitrile

26 Grams (0.125 moles) of isobutyryl-3,4-dimethoxybenzene are put into 100 ml of toluene and then 35 g (0.31 moles) of potassium tert-butoxide are added. After cooling to −10° C., the reaction mixture is added with 33.3 ml (0.31 moles) of ethyl chloroacetate in about two hours. Subsequently the temperature is raised to the value of the room temperature and after another two hours the reaction mixture is added with a solution containing 22 g (0.35 moles) of 90% potassium hydroxide in 100 ml of methanol and is kept under stirring for 6 hours. The reaction mixture is then added with 10 ml of acetic acid, and subsequently with 8.68 g (0.125 moles) of hydroxylamine hydrochloride dissolved in 20 ml of water. The reaction mixture is heated to 60° C. for one hour, then it is acidified to pH 4 by means of concentrated aqueous hydrochloric acid, kept another hour at 60° C. and finally added with water until complete dissolution of the undissolved salts. The layers are separated, the aqueous phase is extracted three times with 50 ml of toluene and then is discarded. The organic phase, together with the toluene extracts, is washed with water, dried over anhydrous sodium sulphate and evaporated to dryness. The oily residue is dissolved in 80 ml of glacial acetic acid and added, under nitrogen atmosphere, with 19.5 ml (0.20 moles) of acetic anhydride. After about 30 minutes the reaction mixture is added with 10 g (0.122 moles) of anhydrous sodium acetate and is heated to 75° C. for 6 hours. The acetic acid is evaporated under vacuum and the residue is treated with a mixture of 100 ml of water and 100 ml of toluene. The mixture is brought to pH 9 by means of a 30% (w/w) aqueous solution of sodium hydroxide, then the layers are separated and the aqueous phase is twice extracted with 75 ml of toluene and then is discarded.

The organic phase is added with the toluene extracts and then is twice washed with 100 ml of water, dried over anhydrous sodium sulphate, filtered and evaporated to dryness under vacuum. The obtained oily residue is distilled under vacuum obtaining 22.3 g of pure nitrile with a yield of 81.4% of the theoretical.

EXAMPLE 7

α-(1-Methylethyl)-3,4-dimethoxybenzeneacetonitrile 24.3 Grams (0.45 moles) of sodium methoxide are added portionwise, in a period of time of one hour, to a mixture of 20.82 g (0.10 moles) of isobutyryl-3,4-dimethoxybenzene and of 48 ml (0.45 moles) of ethyl chloroacetate, while keeping the temperature at about 65° C. The reaction mixture is kept at this temperature for another 2 hours, then it is cooled to room temperature and it is diluted with 50 ml of toluene and 100 ml of water. The layers are separated, the aqueous phase is discarded while the organic phase is washed with 50 ml of water and then is added with a solution containing 30.8 g (0.49 moles) of 90% potassium hydroxide in 150 ml of methanol. After stirring 3 hours at 30° C., the reaction mixture is cooled to 10° C. and diluted with 50 ml of water. The layers are separated, the organic phase is discarded while the aqueous phase is added with 5 ml of acetic acid, heated to 60° C. and added in 30 minutes with 6.25 g (0.09 moles) of hydroxylamine hydrochloride dissolved in 15 ml of water and then with concentrated aqueous hydrochloric acid till pH 6.5. After one hour at 65° C., the pH is brought to 4 with concentrated aqueous hydrochloric acid and the reaction mixture is heated for an additional 2 hours. After cooling to room temperature, the reaction mixture is diluted with 50 ml of toluene, the layers are separated and the aqueous phase is extracted three times with 20 ml of toluene and then is discarded. The organic phase is collected together with the three toluene extracts and then it is washed with 50 ml of water, dried over anhydrous sodium sulphate, filtered and evaporated under vacuum. The oily residue is dissolved in 40 ml of glacial acetic acid and the solution is added portionwise with 9.75 ml (0.10 moles) of acetic anhydride and, after 30 minutes, with 6.5 g (0.08 moles) of anhydrous sodium acetate. The reaction mixture is heated to 80° C. for 6 hours and then the solvent is eliminated under vacuum. The oily residue is treated with 75 ml of water and 75 ml of toluene and the mixture is brought to pH 9.0 by means of a 30% (w/w) aqueous solution of sodium hydroxide. The layers are separated, the aqueous phase is twice extracted with 25 ml of toluene and is then discarded. The organic phase is collected together with the toluene extracts, washed with 50 ml of water, dried over anhydrous sodium sulphate, filtered and evaporated under vacuum.

The obtained oily residue is distilled under vacuum at 2 mm of mercury giving 14.4 g of pure nitrile with a yield of 65.6% of the theoretical.

We claim:

1. A process for the preparation of α-(1-methylethyl)-3,4-dimethoxybenzeneacetonitrile of formula (I):

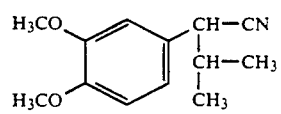

which comprises:
(a) a reacting the isobutyryl-3,4-dimethoxybenzene of formula (II):

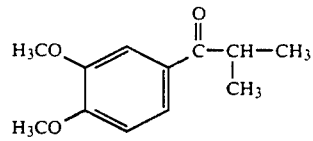

with, for each mole of isobutyryl-3,4-dimethoxybenzene of formula II, from about 0.5 to about 5 molar equivalents of an α-haloester of formula (VII):

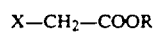

wherein X represents a halogen atom and R represents an alkyl radical, straight or branched, containing from 1 to 6 carbon atoms, in the presence of, for each mole of the compound of the formula II, from about 0.5 to about 5 molar equivalents of a base selected from an alkoxide of an alkali metal of formula (VIII):

wherein Me+ represents a cation of an alkali metal and $R_1$ is an alkyl radical, straight or branched, containing from 1 to 6 carbon atoms, sodium amide or sodium hydride, optionally in the presence of toluene for a period of time of from about 1 to about 24 hours at a temperature between −25° C. and the boiling temperature of the reaction mixture;

(b) subjecting the resulting glycidic ester of formula (III):

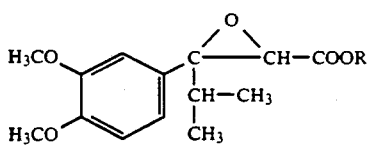

wherein R has the above meaning, to an alkaline hydrolysis at a temperature of from about 0° C. to the boiling temperature of the reaction mixture, for a period of time of from about 1 to 12 hours, to obtain an alkali salt of an epoxyacid of formula (IV):

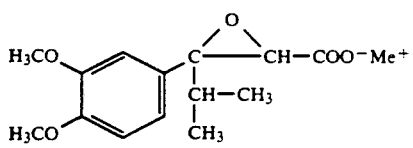

wherein Me+ has the above meaning;

(c) decarboxylating the compound of formula IV, at a temperature of from about 20° C. to the boiling temperature of the reaction mixture for a period of time of from about 1 to about 16 hours, to obtain the α-(1-methylethyl)-3,4-dimethoxy-benzene-acetaldehyde of formula (V):

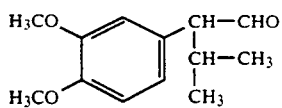

(d) treating said aldehyde of formula V with hydroxylamine hydrochloride at a temperature of from about 0° C. to the boiling temperature of the reaction mixture for a period of time of from about 0.5 to about 16 hours to obtain the α-(1-methylethyl)-3,4-dimethoxybenzeneactaldoxime of formula (VI):

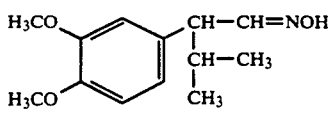

and;

(e) dehydrating said oxime of formula VI by means of acetic anhydride used in an amount of from about 1 to about 4 molar equivalents, based on the amount of oxime of the formula VI, optionally in the presence of sodium acetate and acetic acid, at a temperature of from about 20° C. to the boiling temperature of the reaction mixture, for a period of time of from about 1 to about 48 hours to give the desired nitrile of formula I.

2. A process as defined in claim 1, wherein the compound of formula III is the 2-butyl ester of the 3-(3,4-dimethoxyphenyl)-3-(1-methylethyl) oxiranecarboxylic acid.

3. A process as defined in claim 1 wherein the α-haloester of formula VII is selected from methyl chloroacetate, ethyl chloroacetate and 2-butyl chloroacetate.

4. A process as defined in claim 1 wherein the alkoxide of formula VIII is selected from sodium methoxide, potassium 2-butoxide, sodium 2-butoxide and potassium tert-butoxide.

* * * * *